United States Patent [19]

Chang

[11] Patent Number: 5,281,699

[45] Date of Patent: *Jan. 25, 1994

[54] TREATING B CELL LYMPHOMA OR LEUKEMIA BY TARGETING SPECIFIC EPITOPES ON B CELL BOUND IMMUNOGLOBULINS

[75] Inventor: Tse W. Chang, Houston, Tex.

[73] Assignee: Tanox Biosystems, Inc., Houston, Tex.

[*] Notice: The portion of the term of this patent subsequent to Nov. 9, 2010 has been disclaimed.

[21] Appl. No.: 531,787

[22] Filed: Jun. 1, 1990

[51] Int. Cl.$^5$ .................. A61K 37/02; C07K 7/08; C07K 7/10

[52] U.S. Cl. .................. 530/405; 530/324; 530/325; 530/326; 530/327; 530/328; 530/329; 530/387.1

[58] Field of Search .............. 530/387, 405, 324, 325, 530/326, 327, 328, 329, 387.1

[56] References Cited

PUBLICATIONS

Ishida, N. et al., *EMBO Journal*, 1(9):1117–1123, 1982.
Cheng, H. et al., *Nature*, 296:410–415, Apr. 1982.
Tyler, B. et al., *Proc. Natl. Acad. Sci.*, 79:2008–2012, Mar. 1982.
Rogers, J., *Cell*, 26:19–27, Oct. 1981.
Honjo, et al., *Cell*, 18:559–568, 1979.
Manning, D. D., "Heavy Chain Isotype Suppression: A Review of the Immunosuppressive Effects of Heterologous Anti-Ig Heavy Chain Antisera" J. Reticulo. Soc. 18:63–86. (1975).
Manning, D. D. et al. "Suppression of Reaginic Antibody (IgE) Formation in Mice by Treatment with Anti-$\mu$ or Anti-$\sigma$ Antiserum" J. Exp. Med. 144:288–293 (1976).
Bazin, H. et al. "Differential Effect of Neonatal Injections of Anti-$\mu$ Antibodies on the Synthesis of IgM, IgE, IgA, IgG1, IgG2a, IgG26 and IgG2c Immunoglobulin Classes" J. Immunol. 121:2038–2087 (1978).
Tahghi-Kilani, R. et al. "The Role of Humoral Immunity in Cryptosporidium spp. Infection Studies with B Cell-Depleted Mice" J. Immunol. 145:1571–1576 (1990).
Word et al. "The Murine Immunoglobulin $\alpha$ Gene Expresses Multiple Transcripts from a Unique Membrane Exon" (particularly; p. 895, 2nd column) EMBO Journal 2:887–898 (1983).

*Primary Examiner*—Lester L. Lee
*Attorney, Agent, or Firm*—Eric P. Mirabel

[57] ABSTRACT

Membrane anchoring peptides which are part of the heavy chain of an associated immunoglobulin (IgM, IgD, IgA, IgE, or IgG), span the cell membrane lipid bilayer of B cells thereby affixing the associated immunoglobulin to the cell membrane surface. The extracellular segments of these peptides are unique for different isotypes, but tend to be very similar among different subclasses of a particular isotype. The extracellular segments form in whole or in part an epitope unique to the B cells which produce each isotype. These membrane-bound immunoglobulin isotype-specific ("migis") extracellular epitopes are not present on the secreted, soluble form of the immunoglobulins, which are not bound to the cell surface by the membrane anchoring peptides. The antibodies of the invention (and other related products) bind the extracellular migis epitopes. Tumorous B cells which produce particular isotypes, whether associated with B cell lymphoma and B cell leukemia, can be destroyed when they are bound by such an antibody (or by a derivative product of such an antibody), by any of a number of well-known mechanisms.

3 Claims, 13 Drawing Sheets

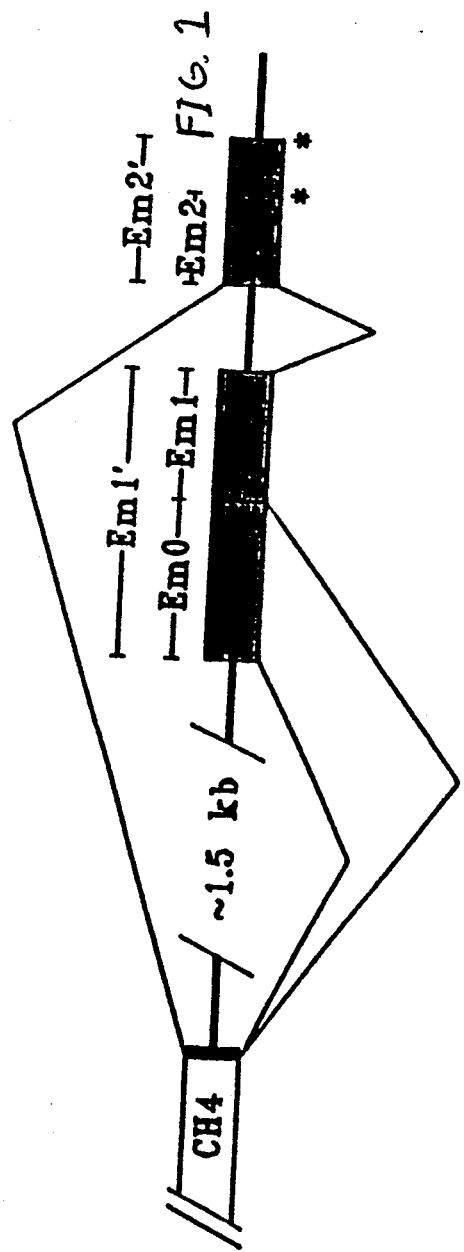

```
                                              ↙— εm1 exon (122 N)
···CH4 domain··· GTG·TCT·GTA·AAT·CCC·GAG·CTG·GAC·
                  V   S   V   N   P   E   L   D GTG·TGC·GTG·GAG·GAG·GCC·GAG·GGC·GAG·GCG·CCG·TGG·
 V   C   V   E   E   A   E   G   E   A   P   W ACG·TGG·ACC·GGC·CTC·TGC·ATC·TTC·GCC·GCA·CTC·TTC·
 T   W   T   G   L   C   I   F   A   A   L   F CTG·CTC·AGC·GTG·AGC·TAC·AGC·GCC·GCC·CTC·ACG·CTC·
 L   L   S   V   S   Y   S   A   A   L   T   L ↙ εm2 exon (84 N)
CTC·ATG·GTG·CAG·CGG·TTC·CTC·TCA·GCC·ACG·CGG·CAG·
 L   M   V   Q   R   F   L   S   A   T   R   Q GGG·AGG·CCC·CAG·ACC·TCC·CTC·GAC·TAC·ACC·AAC·GTC·
 G   R   P   Q   T   S   L   D   Y   T   N   V

CTC·CAG·CCC·CAC·GCC·TAG·
 L   Q   P   H   A   ***
```

Figure 2A

```
                                                      ₧m0 exon (156 N)
···CH4 domain···GTG·TCT·GTA·AAT·CCC·GGG·CTG·GCT·
                 V   S   V   N   P   G   L   A GGC·GGC·TCC·GCG·CAG·TCC·CAG·AGG·GCC·CCG·GAT·AGG·
 G   G   S   A   Q   S   Q   R   A   P   D   R GTG·CTC·TGC·CAC·TCC·GGA·CAG·CAG·CAG·GGA·CTG·CCG·
 V   L   C   H   S   G   Q   Q   Q   G   L   P AGA·GCA·GCA·GGA·GGC·TCT·GTC·CCC·CAC·CCC·CGC·TGC·
 R   A   A   G   G   S   V   P   H   P   R   C CAC·TGT·GGA·GCC·GGG·AGG·GCT·GAC·TGG·CCA·GGT·CCC·
 H   C   G   A   G   R   A   D   W   P   G   P ₧m1 exon (122 N)
CCA·GAG·CTG·GAC·GTG·TGC·GTG·GAG·GAG·GCC·GAG·GGC·
 P   E   L   D   V   C   V   E   E   A   E   G GAG·GCG·CCG·TGG·ACG·TGG·ACC·GGC·CTC·TGC·ATC·TTC·
 E   A   P   W   T   W   T   G   L   C   I   F GCC·GCA·CTC·TTC·CTG·CTC·AGC·GTG·AGC·TAC·AGC·GCC·
 A   A   L   F   L   L   S   V   S   Y   S   A ₧m2 exon (84 N)
GCC·CTC·ACG·CTC·CTC·ATG·GTG·CAG·CGG·TTC·CTC·TCA·
 A   L   T   L   L   M   V   Q   R   F   L   S GCC·ACG·CGG·CAG·GGG·AGG·CCC·CAG·ACC·TCC·CTC·GAC·
 A   T   R   Q   G   R   P   Q   T   S   L   D TAC·ACC·AAC·GTC·CTC·CAG·CCC·CAC·GCC·TAG·
 Y   T   N   V   L   Q   P   H   A  ***
```

Figure 2B

```
                                              ∊m2' exon (137 N)
···CH4 domain···GTG·TCT·GTA·AAT·CCC·GGT·GCA·GCG·
                 V   S   V   N   P   G   A   A GTT·CCT·CTC·AGC·CAC·GCG·GCA·GGG·GAG·GCC·CCA·GAC·
 V   P   L   S   H   A   A   G   E   A   P   D CTC·CCT·CGA·CTA·CAC·CAA·CGT·CCT·CCA·GCC·CCA·CGC·
 L   P   R   L   H   Q   R   P   P   A   P   R CTA·GGC·CGC·GGG·CAC·TCA·CGC·TCC·ACC·AGG·CCC·AGC·
 L   G   R   G   H   S   R   S   T   R   P   S

TTT·TTC·TCT·GCC·AGC·GCC·TGA·
 F   F   S   A   S   A   ***
```

| | |
|---|---|
| CCCAGACCAGAGCAAGGTCCTCGCACACGTGAACACTCCTCGGACACAGGCCCCCACGAG | 60 |
| CCCCACGCGGCACCTCAAGGGCCCACGAGCCTCTCGGCAGCTTCTCCACATGCTGACCTG | 120 |
| CTCAGACAAACCCAGCCCTCCTCCTCACAAGGGTTGCCCCTGCAGCCGCCACACACAC | 180 |
| AGGGGATCACACACCACGTCACGTCCCTGCCCTGGCCCAAGCGTTCCCAGTGCCGGCCCT | 240 |
| TCCCTGCAGGCTGGGGTCACATGAGGTGTGGGCTTCACCATCCTCGCTCCTCTGGGCCTC | 300 |
| AGGGAGGGACACGGGAGACGGGGAGCGGGTCCTGCTGAGGCCAGGTCGCTATCTAGGGCC | 360 |
| GGGTGTCTGGCTGAGCCCCGGGGCCAAAGCTGGTGCCCAGGGCGGGCAGCTGTGGGGAGC | 420 |
| TGACCTCAGGACATTGTTGGCCCATCCCGGCCGGGCCCTACATCCTGGGGCCCCGCCACA | 480 |
| GAGGGAATCACCCCCAGAGGCCCAAGCCCAGGGGGACACAGCACTGATCCACCCCCTTCC | 540 |
| TGTCCAG<u>AGCTGCAACTGGAGGAGAGCTGTGCGGAGGCGCAGGACGGGGAGCTGGACGGG</u> | 600 |
| <u>CTGTGGACGACCATCACCATCTTCATCACACTCTTCCTGTTAAGCGTGTGCTACAGTGCC</u> | 660 |
| <u>ACCGTCACCTTCTTC</u>AAGGTCGGCCGCACGTTGTCCCCAGCTGTCCTTGACATTGTCCCC | 720 |
| CATGCCTGTACAAACTGTCTCTGACACTGTCCACAGGCTGTCCCCACCTGTGCCCTGACG | 780 |
| CTGTCCCCCATGCTCTCACAAACTGTCCCTGACATTGTCCCCAATGCTGCCCCCACCTGT | 840 |
| CCAACAGTGTCCCCCAGGCTCTCCCCACATGTCCCCGACACTGTCCCCATGCTGTCCCC | 900 |
| ATCTGTCCCCAACACTGTCCCCCACCCTGTCCCCTTTGTCCCCAACACTGTCCCCCACA | 960 |
| GTTTCCACCTGTCCCTGACACTCCCCCATGCTTTCCCCACCTGTCCCTGACACCATCCCC | 1020 |
| CACTGTCCCCATAGTTCCTGGCCTGTCCCCCACGCTGTCCCCTACAGTACCTGGCACTGT | 1080 |
| CCCCCATGCTGTCCCCTCCTGTTATGAAACCCTGTCCCACATGCTGTCCCCACCTGTCCG | 1140 |
| TGACAATATCCCCCACACTGTCCCCACCTGTCCCCGACACTCTCCTCCACGTTGTTCTTA | 1200 |
| CCTAAACCCGACACTTCCTCCATGCTGTCCCACCCATCTCCGACACTGTACCCA | 1254 |

Figure 3B

```
TCCCCTATAATCCCTACACTGTCCCCCACACCGTCCCCTCCTGTATGCACCACTGTCCCC       60
CATGCTGTCCCCACCTGTCCCTGATGCTGTCCTCCACACATCCCCACCTCTCCCTACACT      120
GTCCCCATCTCTCCCCAACACTCTCCTCCTCCATGCTGTCCTCAACTGTCCCCAACACTC      180
TTCCACACTCTGTCTCCACCTGTCCCTGACACTGTCCCCCTACACTGTCCTCACCTGTGT      240
CTGACACTGTCCCCCACGCTGTCCCCACCTGTCCCTGAACGCTGTCTTCTGTGCTGTCCA      300
CATGCTGTTGGAGCCCTGGCTCTGCTCTCTATCACCAAGCCTCAGAGCAGGCAGTGGTGA      360
GGCCATGGCACCTGGGTGGCATGAGGGGCCGGATGGGCCTCAGGGGCAGGGCTGTGGCCT      420
GCGTGGACTGACGGGTGGGTGGGCCTTGGGGGCAGAGAGGTGGCCTCAGTGCCCTGAGGG      480
GTGGGTGGGGCTCGGGGGCAGGGCTGTGGCCTCGCTCACCCCTGTGCTGTGCCTTGCCTA      540
CAGGTGAAGTGGATCTTCTCCTCGGTGGTGGACCTGAAGCAGACCATCATCCCCGACTAC      600
AGGAACATGATCGGACAGGGGGCCTAGGGCACCCTCTGCGGGGTGTCCAGGGCCGCCCAG      660
ACCCCACACACCAGCCATGGGCCATGCTCAGCCACCACCCAGGCCACACCTGCCCCCGAC      720
CTCACCGCCCTCAACCCCATGGCTCTCTGGCCTCGCAGTTGCCCTCTGACCCTGACACAC      780
CTGACCATAGACGGTCTACCCCAGACCTCCGCCAGTTGGTGCATGCAGGGGCATGGGG      838
```

Figure 4A
```
γ1    cagcactgaccacccccttcctgtccaGAGCTGCAACTGGAGGAGAGCTGTGCG
      GAGGCG
γ2    --t-t---------a-------------------------------------TGC
      ------
γ3    --------------------------------------------------------
      ------
γ4    --------------------------------------------------------
      ------

γ1    CAGGACGGGGAGCTGGACGGGCTGTGGACGACCATCACCATCTTCATCACACTC
      TTCCTG
γ2    -----------------------------C--------------------------
      ------
γ3    --------------------------------------------------------
      ------
γ4    --------------------------------------------------------
      ------

γ1    TTAAGCGTGTGCTACAGTGCCACCGTCACCTTCTTCAAGgtcggccgcacgttg
      tcccca
γ2    C------------------A----------------t-------------------
      -------
γ3    --------------------------------------------------------
      -------
γ4    C----------------------------------------------------ca
      t-gt--c
γ1    gctgtccttga--/ /--cccctgtgctgtgccttgcctacagGTGAAGTGGA
      TCTTCTC
γ2    ------------/ /-----------------------------------------
      ------
γ3    ------------/ /-----------------------------------------
      ------
γ4    a-c--gg-cct--/ /----------------------------------------
      -------

γ1    CTCGGTGGTGGACCTGAAGCAGACCATCATCCCCGACTACAGGAACATGATCG
      GACAGGG
γ2    ---A------------------G---------------------------------A
      -G-----
γ3    -----------------------------------------T------------T-
      -G-----
γ4    ---A------------------G-------------------------------AA
      -G-----

γ1    GGCCTAGggcaccctctgcggggtgtccaggg
γ2    ------------------t-------------
γ3    ------------------------.-------.----c
γ4    --------------------------------
```

Figure 4B

*extracellular segment*

```
γ1    ELQLEESCAEAQDGELDG| LWTTITIFITLFLLSVCYSATVTFFKVKWIFSSVVD
      LKQTII            |
γ2    ------------------|----------------------I---------------
      -----V            |
γ3    ------------------|-----------------------------------------
      ------            |
γ4    ------------------|-----------------------------------------
      -----V

γ1    PDYRNMIGQGA
γ2    -------R---
γ3    -----------
γ4    -------R---
```

Figure 5A

```
         CH3 Domain                            |M1 Exon
......CAGAAGAGCCTCTCCCTGTCCCCGGAGCTGCAACTGGAGGAGAGCTGTGCGGAG GCGCAGGACGGGGAGCTGGACGGGCTGTGGACGACCATCACCATCTTCATCACACTCTTC
                                              |M2 Exon
CTGTTAAGCGTGTGCTACAGTGCCACCGTCACCTTCTTCAAGGTGAAGTGGATCTTCTCC
       |3' Untranslated region
GCCTAGGGCCACCCTCTGCGGGGTGTCCAGGGCCGGCCCAGACCCCACACACCAGCCATG

GGCCATGCTCAGCCACCACCCAGGCCACACCTGCCCCGTCCTC......
```

Figure 5B

```
                                        Secreted form
                                   3' untranslated region
              donor
CH3   domain----TCCCTGTCCCCGG|GTAAATGAgtgcgacggccggcaagccccg
              ctccccggg----
```

```
                                   acceptor
              ----ccttcctgtccag|AGCTGCAACTGGAG----
M1    exon
              donor
              ACCGTCACCTTCTTCAAG|gtcggccgcacgttg----
```

```
                                   acceptor
              ----cttgccttgcctacag|GTGAAGTGGATCTTC----
M2    exon   GGGGGCCTAGggcaccctctgcggggtgtccagggccgc
             cag----
                                        Membrane bound
                                   3' untranslated region
```

Figure 6
    1 ctcccatcccttcctaagcccaactaggacccaaagcatagacagggaggggccacgtgg
   61 ggtggcatcagaagCAGGCCAGTGAGACAGGGCCTGCCCAGGGCCCTCTGCATGCCTCTG
  121 GTTCTGCCTGGGCTCCCAGGAGTGTAAGAACAGTCCCACAACCACTGTGGGGACACCTGG
  181 CACTCAGACTCCCACAAGGGGGCAGTGGGCCCCTGCTCGTGCCTTAGACATCTTCCGGG
  241 CCTCCCCAGGGCCCCCGCCTTCTGGCTGCCTCCCTCTGCTCTCAGGGCCAAGGTGAGGT
  301 GGAGGCCACTGTCACCCCTGAGGGTCCAGTCACCAGAGGGTAATTGAGAGCAACAGGTCA
  361 CTCGGGGAAGCCCTGCCACAGAGAAGCCCTCCAGCCCATGGGACCCAGGACCTGGCCCAG
  421 GGGAGGGGCTTTTAAAGAGAGGGGGAAAGAGGGAGAATCAACAGATGAGGGGCTGAACCA
  481 GCAGACAGAGATCAGGCAGACACATGGGTAGATCCTAGGACATATAATGAATGGATGGGT
  541 GGATGGAGGATTGGTAGACGGAGGATGGATGGGTGGGTAAATGGCTGGATGGAGGATGGA
  601 CAGATGGATATATGATGGATGGATGAAGGACGGGTGGATGGAGGATGGATGAGTGGATGA
  661 ATGAAGGATGGAAGATGGATGGATGGATGGGTGGATGGACTGATGGATGATGGATGGATG
  721 GATGGATGGATGATGGATGGATGGGTAGGCGGATGGAGGATGGAAGGTGGATGGAGGAT
  781 GGAAGATAGATGGAGGGGTGAATGGAGGATGGGTGGACTGACGGAGGATTGAGGATACTG
  841 GGGTGGGTGGGTGGGTAGATCTATGGAGGATAGGTGTATGGAAGATAATTGGATGGAGAA
  901 TTGCTTTATGAATGGATGAATGAAGAGATGGAAAATAGCTTTATAGATGGATGGGTGAAT
  961 GGATGGATGGATAGATGGAAGAAGGATGAATGGATGGAAAATAGCTTTATAGATATATGG
 1021 GTGGATATTTAAGTGATAGCCTAACATTAATAGATGAATGGAGGATGAATGGTTGGGTGA
 1081 GTGGGTAGGAGTGTTACTGATGGAGGGGTGGATATACGGATAATAGCTTTATAGATGGAT
 1141 CCGGGACCCAGTCACTGAATACGTGGCTGGGACTGAGACGGGGTGGGGTGGGAGGGGCGG
 1501 GAGGGTACCTCGGGCTCAAGCTTCCCTTGGAGAAGCAGATGGTGTCCACTTTCTGCCCTG
 1561 CCAAGTCTCTCCCTGAAGTGCCCTAAGAATGTCAAAGACAGAAGGTCCCAGCCCCTCACC
 1621 TGGGACTCTGCCTCCTCATCCTCCCTGGGGGAGTCTCAGGCCTTAGATGGGGACCCAGAC
 1681 CCCACTGTCCCCAGACCCCAAGGAAGCATAGCCGCTGTTCACACGAGTCTGGGCCTGGCA
 1741 GGCTCTTGCTCTGTTGCAGATTGGCAGATGCCGCCTCCCTATGTGGTGCTGGACTTGCCG
         /g  s   c   s   v   a/D   W   Q   M   P   P   P   Y   V   V   L   D   L   P 1801 CTCACCCTCTTCCTGCTGAGCCTGTTCTATAGCACAGCACTGACCGTGACCAGCCTCCGG
       Q   E   T   L   E   E   E   T   P   G   A   N   L   W   P   T   T   I   T   F 1861 CTCACCCTCTTCCTGCTGAGCCTGTTCTATAGCACAGCACTGACCGTGACCAGCCTCCGG
       L   T   L   F   L   L   S   L   F   Y   S   T   A   L   T   V   T   S   V   R 1921 GGCCCATCTGGCAACAGGGAGGGCCCCCAGTACTGAGCGGGAGCCGGCAAGGCACAGGTG
       G   P   S   G   N   R   E   G   P   Q   Y 1981 GGAGCCCAGGAGGGGGATGAGCCCACAGTGGATGAGGTGGGCTGCAGTGCTTGGCTAAGA
 2041 GGAGAGCACCACCTGCTCCCACTGTGGGGGACGTGCTCTCCTGGGGGCCCTTCACAGA
 2101 CACTGAGGACACGCGCAGGCCCAGGGTCAGGGCTGAGCTTCCCTCCAGTGCAGTAACGAG
 2161 GATTCCGTCCAGGCTCCCATGAGCAGGCCAGGGCTGAGACAGAGGGCGTTGGCAAAGATG
 2221 CTGCTCCTTCAGGCTGTGACCCCTCTGTCTTTGCAGGGAGGAAGTGTGGAGGAACCTCTT
 2281 GGAGAAGCCAGCTATGCTTGCCAGAACTCAGCCCTTTCAGACGTCACCGACCCGCCCTTA
 2341 CTCACATGCCTTCCAGGTGCAATAAAGTGGCCCCAAGGAAAA

Figure 7A

```
                                              40                                     80
hu α₁   - gctcttgctc tgttgcagAT TGGCAGATGC CGCCTCCCTA TGTGGTGCTG GACTTGCCGC AGGAGACCCT GGAGGAGGAG
           ||||||||| ||||||||||  |||||||||| |||||||||| |||||||||| |||||||||| |||||||||| ||||||||||
hu α₂   - gctcttgctg tgttgcagAT TGGCAGATGC CGCCTCCCTA TGTGGTGCTG GACTTGCCGC AGGAGACCCT GGAGGAGGAG
                                 ||         |||||||||| |||| ||||| ||||  |||| |||| ||||  ||||| |||
mu α    - ---------- ---------AA CGTCAAGAGC CACTTTCCTA TGTGCTACTG GACCAGTCAC AAGACATCCT GGAGGAAGAG 120                                    160
hu α₁   - ACCCCCGGCG CCAACCTGTG GCCCACCACC ATCACCTTCC TCACCCTCTT CCTGCTGAGC CTGTTCTATA GCACAGCACT
           |||||||||| |||||||||| |||||||||| |||||||||| |||||||||| |||||||||| |||||||||| ||||||||||
hu α₂   - ACCCCCGGCG CCAACCTGTG GCCCACCACC ATCACCTTCC TCACCCTCTT CCTGCTGAGC CTGTTCTATA GCACAGCACT
           ||  |||||| ||  |||||| ||||||||   |||||| ||  |||||| ||| ||| ||||||  |||||||| | ||||||||||
mu α    - GCCCCAGGTG CCAGCCTGTG GCCCACCACT GTGACCTTCC TCACCCTCTT CCTACTGAGC TTGTTCTACA GCACAGCACT 200
hu α₁   - GACCGTCACC AGCGTCCGGG GCCCATCTGG CAACAGGGAG GGCCCCCAGT ACTGA
           |||||| ||| ||||| |||| |||||||||| |||| ||||| |||||||||| |||||
hu α₂   - GACCGTGACC AGCGTCCGGG GCCCATCTGG CAAGAGGGAG GGCCCCCAGT ACTGA
           ||  || ||| |||||  ||| ||||| ||||  || |||| ||  |||| |||| |||||
mu α    - CACTGTTACA ACTGTTCGAG GCCCGTTTGG CAGCAAAGAG GTCCCCCAGT ACTGA
```

Figure 7B

```
                    extracellular segment
                              40
hu α₁ -  gscsvaDWQM PPPYVVLDLP OETLEEETPG ANLWPTTITF LTLFLISLFY STALTVTSVR GPSGNREGPQ Y
hu α₂ -  gsccvaDWQM PPPYVVLDLP OETLEEETPG ANLWPTTITF LTLFLISLFY STALTVTSVR GPSGKREGPQ Y
mu α  - ------EROE PLSYVLLDQS QDTLEEEAPG ASLWPTTVTF LTLFLISLFY STALTVTIVR GPFGSKEVPQ Y
```

TREATING B CELL LYMPHOMA OR LEUKEMIA BY TARGETING SPECIFIC EPITOPES ON B CELL BOUND IMMUNOGLOBULINS

FIELD OF THE INVENTION

The invention relates to treatment of human B cell lymphoma or leukemia through antibody targeting of epitopes present on B cell membrane-bound immunoglobulins, but not present on the secreted form of the immunoglobulins.

BACKGROUND OF THE INVENTION

B-cell lymphoma is a generally fatal cancer of the immune system. It afflicts about 100,000 people in the United States alone, and its incidence is increasing at about 7% per annum. This increase results in part from the corresponding increase in Acquired Immune Deficiency Syndrome ("AIDS"). The high grade B cell non-Hodgkin's lymphoma, which is a particularly aggressive lymphoma, is often a sequelae of AIDS; or HIV-1 infection.

By way of background, it is noted that malignant lymphomas are a heterogeneous group of neoplasms, generally originating in the lympho-reticular system. They are usually observed as lymph node tumors. Hodgkin's disease is a subgroup of the lymphomas. The cell of origin in Hodgkin's disease is believed to be derived from the monocyte-histiocyte series. The other lymphomas, which can affect either the T cell or the B cells, are referred to as non-Hodgkin's lymphomas. The non-Hodgkin's T and B cell lymphomas are divided into the high grade and low grade types, the former being more pathogenic than the latter.

Resting B cells, which are immunocompetent but not yet activated, express Igm and IgD. Once activated, these B cells can express any of the five immunoglobulin isotypes, (IgD, IgM, IgA, IgE or IgG). The non-Hodgkin's B cell lymphomas are generally associated only with B cells which express one particular isotype. IgM-expressing B cells are most often affected, leading to so-called small cleaved type lymphomas, characterized as such due to the appearance of the affected cells. However, B cells which express any of the other isotypes can also be affected.

Leukemia is best defined as the proliferation of a clone of abnormal hematopoietic cells. Myeloid leukemias affect the descendants of the myeloid lineage, whereas the lymphocytic leukemias involve abnormalities in the lymphoid lineage. The lymphocytic leukemias can be divided further into those affecting T cells and those affecting B cells. Leukemias of either type can be acute or chronic, the acute form being more aggressive. Without treatment, however, even the chronic leukemias can be fatal.

Several conventional methods are used to treat B cell lymphomas and leukemias. However, because these diseases respectively spread throughout the lymphatic and circulatory systems, conventional treatment is difficult. The tumors which arise in the B cell lymphomas are not amenable to removal by surgery. While radiation therapy may kill the individual lymphoma tumors, it will also damage the healthy tissue surrounding the malignancies.

Chemotherapy can be used to treat the B cell lymphomas or leukemias. The B cell leukemias are usually treated with chemotherapy because they do not produce readily identifiable tumors. The side effects of chemotherapy, however, are often debilitating, with damage to critical fast-growing cell such as blood cells in the bone marrow. Further, certain B cell lymphomas tend to rebound from chemotherapy in more aggressive forms.

Most B cell lymphomas (and, as noted above, substantially all the leukemias) are monoclonal, meaning that all tumor cells in a patient are derived from one cell, and therefore, bear the same antibody idiotype on the cell surface. This fact has led one group, IDEC Pharmaceuticals Corp., to attempt treatment of B cell lymphomas through targeting the affected B cells with antibodies which bind only to the idiotypes produced by the affected B cells. Typically, malignant cells derived from B cells at late stages of differentiation secrete antibody and also express antibody on their cell surface. The IDEC antibodies bind to both the secreted and cell-bound idiotypes. When the IDEC antibodies bind the cell-bound idiotypes, the associated B cells are somehow destroyed by the immune system's suppressive or cytolytic mechanism.

The IDEC approach avoids some disadvantages of conventional therapy, particularly the debilitating side effects of chemotherapy, but it also suffers from significant drawbacks. At first, it was necessary to custom-make the IDEC antibodies for each patient. It can take several months to make mouse (or reurine) antibodies. It is often desirable, however, to make chimeric or humanized antibodies which are less immunogenic than mouse antibodies. With aggressive high grade lymphomas, the patient would not survive long enough to produce the appropriate less immunogenic antibodies. Even with less aggressive, low grade lymphomas, the time to production is sufficiently long so that there could be an appreciable decline in the patient's health. Further, the production process is very labor intensive and expensive.

It was later discovered that certain tumor-associated idiotypes are common to some patients with B cell lymphoma. This meant that some of IDEC's antibodies would be effective among different patients. Even though it was then no longer necessary to custom make the product in all cases, several disadvantages remained.

First, the developers of the IDEC therapy have recognized that it is only effective in patients which secrete limited amounts of the target antibodies. See S.L. Brown et al., "Antiidiotype Antibody Therapy of B-Cell Lymphoma" Vol. 16, No. 3, pp. 199-210 *Seminars in Oncology (June* 1989). In patients which secrete large amounts of antibody, much of the IDEC antibodies which are -administered will bind to these endogenous secreted antibodies, and thus, the administered antibodies will not significantly affect the tumorous B cells. It is known that the tumorous B cells in patients having high grade lymphomas, and who are particularly in need of an immediately effective treatment, secrete large amounts of antibody. Thus, the IDEC therapy may be least effective in those who need it most.

The S.L. Brown et al. group also recognized that the IDEC therapy selects for idiotype-negative tumor cells. These tumor cells do not react with the IDEC antibodies, resulting in new tumors which cannot be treated with the IDEC methods. This group also combined the IDEC therapy with administration of 1@ba interferon. This appeared to yield a higher response rate than antibody administration alone, yet it also appeared to exert an even stronger selection pressure for the idiotype-negative tumor cells.

In an alternative approach, some members of this group tried using a radiolabeled antibody to target the tumor cells. The radiolabeled antibody is itself cytotoxic. One disadvantage noted by this group is that myelosuppression occurred in all patients tested three to five weeks after treatment. An additional disadvantage of this therapy which was not noted is inherent in the use of radioisotopes. The patient's feces, urine, saliva, sweat, and other bodily secretions will all become radioactive as a result of the treatment. Disposal of these radioactive products presents major problems.

It seems that administering antibodies which react only with cell-bound idiotypes, which idiotypes are common to a majority of patients and are not subject to selection which yields an idiotype-negative tumor cell, would be an effective therapy for both B cell lymphoma and B cell leukemia. Such antibodies would avoid the disadvantages of radioimmunotherapy, chemotherapy, and of the IDEC approach.

SUMMARY OF THE INVENTION

The invention includes epitopes unique to the cell-bound forms of various immunoglobulin isotypes, antibodies and derivative products which target these epitopes, and the use of such antibodies and other products in therapy of B cell lymphoma or B cell leukemia. The human immunoglobulin isotypes are IgG (having four subclasses), IgA (having two subclasses), IgM, IgD, and IgE. IgG causes opsonization and cellular cytotoxicity and crosses the placenta, IgA functions on the mucosal surface, IgM is most effective in complement fixation, and IgE mediates degranulation of mast cells and basophils. The function of IgD is still not well understood. The heavy chains of the isotypes IgG, IgA, IgM, IgD and IgE are respectively designated the gamma, $\alpha, \mu, \delta,$ and $\epsilon$ chains.

The heavy chains of the immunoglobulins contain membrane anchoring peptides which span the cell membrane lipid bilayer, thereby affixing the associated immunoglobulin to the cell membrane surface. The extracellular portions of these peptides are unique for different isotypes, but tend to be very similar among different subclasses of a particular isotype. The extracellular segment forms in whole or in part an epitope unique to the B cells which produce each isotype. These membrane-bound immunoglobulin isotype-specific ("migis") extracellular epitopes are not present on the secreted, soluble form of the immunoglobulins, which are not bound to the cell surface by the membrane anchoring peptides.

The antibodies and other related products of the invention bind to the migis epitopes which are present on the B cell surface. The B cells can then be eliminated or controlled by a number of immune mechanisms.

As noted above, the tumorous B cells in B cell lymphoma and leukemia are monoclonal, and thus all express the same isotype. By targeting the extracellular migis epitopes specific to the isotypes of the tumorous B cells, all the tumorous B cells can be destroyed. Although many normal B cells which produce the targeted isotype will also be destroyed, the other components of the immune system (and the other isotypes) will remain intact. The adverse effect on the immune response resulting from affecting one isotype should be minimal. It can be appreciated that this presents a tremendous potential therapy for both B cell lymphoma and B cell leukemia.

Because the migis epitopes are not present on the secreted form of the various isotypes, they should be as effective in patients with B cell tumors which secrete significant amounts of antibody as in those whose B cells produce limited amounts of secreted antibody, or none at all. Further, because the membrane anchoring peptides are not associated with a variable portion of the respective immunoglobulins, they are not likely to mutate to an idiotype-negative form when antibodies of the invention (or related products) are administered.

The antibodies of the invention include both polyclonal and monoclonal antibodies. To avoid or minimize an immunogenic reaction to the antibodies administered, chimeric antibodies, which are a combination of an animal variable binding region and a human constant region, can be used. Alternatively, human antibodies can be used. The animal, chimeric or human antibodies may by used in direct therapy or in active immunization. Several other derivative and related products of the antibodies of the invention, described further below, can also be used in therapy.

The invention will now be further described with reference to the drawings.

BRIEF DESCRIPTION OF THE DRAWINGS

FIG. 1 shows three different mRNA splicings which create three different isoforms (I; II and III) of the membrane anchoring peptide of human $\epsilon$ chain.

FIG. 2A shows the peptide-coding nucleotide sequence and the deduced amino acid sequence of isoform I of the membrane anchoring peptide of human $\epsilon$ chain.

FIG. 2B shows the peptide coding nucleotide sequence and the deduced amino acid sequence of the membrane anchoring peptide of isoform II of human $\epsilon$ chain.

FIG. 2C shows the peptide-coding nucleotide sequence and the deduced amino acid sequence of isoform III of human $\epsilon$ chain.

FIG. 3A shows the genomic DNA sequence of a segment of human gamma-1 chain, the sequence of a first membrane exon which is proposed to encode for the membrane anchoring peptide being underlined, and the flanking nucleotide sequences not being underlined.

FIG. 3B shows the genomic DNA sequence of a segment of human gamma-1 chain, the sequence of a second membrane exon which is proposed to encode for the membrane anchoring peptide being underlined, and the flanking nucleotide sequences not being underlined.

FIG. 4A shows the nucleotide sequences of the two membrane exons of human gamma-1 chain shown in FIGS. 3A, 3B (some of the flanking sequences are shown by lower case letters), as well as the corresponding nucleotide sequences for human gamma-2, gamma-3, and gamma-4 chains.

FIG. 4B shows the deduced amino acid sequences encoded for by the membrane exons shown in FIG. 4A, the proposed extracellular segment being indicated.

FIG. 5A shows the sequence of a segment of CDNA of human gamma-1 chain from mRNA of IM9 cells, linking the CH3 domain to the membrane exon shown in FIG. 3A, to the membrane exon shown in FIG. 3B, to the 3' untranslated region.

FIG. 5B shows the splicing donor/acceptor sites of the segment of CDNA shown in FIG. 5A.

FIG. 6 shows the amino acid and nucleotide sequence of the membrane exon of two isoforms of human $\alpha 1$ membrane anchoring peptide (one isoform including the amino acids shown in lower case letters) as well as about 1,700 bp of the 5' flanking sequence and about 500 bp in the 3' untranslated region.

FIG. 7A shows the nucleotide sequence of the membrane exon shown in FIG. 6 for human α1 and α2, as well as the corresponding sequence from reurine α chain.

FIG. 7B shows the amino acid sequences encoded by the exons shown in FIG. 7A, the proposed extracellular segments being underlined.

DETAILED DESCRIPTION OF THE PREFERRED EMBODIMENTS AND THEIR MANNER AND PROCESS OF MAKING AND USING

Membrane anchoring peptides are parts of the heavy chains of the associated isotypes, and anchor the isotypes to the cell surface. These anchoring peptides have lengths ranging from 41 to 130 amino acids and can be divided into three segments, each segment located differently with respect to the plasma membrane. The middle segments of about 25 uncharged and hydrophobic residues are in the membrane lipid bilayer. The C-terminal hydrophilic segments of 3 to 28 residues are intracellular. The segments towards the N-terminus contain about 13 to 67 amino acid residues, are highly acidic and hydrophilic and are on the extracellular surface of the plasma membrane. Because the latter segments towards the N-terminus are extracellular, they are exposed and accessible to antibodies and can be targeted, thereby providing a means of destroying B cells producing a particular isotype. These extracellular segments form, in whole or in part, epitopes designated herein as the extracellular migis epitopes.

The proposed sequences of the membrane anchoring peptides of IgE, IgG (subclasses 1 to 4), and IgA (subclasses 1 and 2) were determined by the methods outlined below. The sequences of the membrane anchoring peptides of IgM and IgD were previously known.

Peptides containing the extracellular migis epitopes, or segments or immunologic equivalents of these peptides, can be used as immunogens. Such immunogenic peptides can be synthesized by conventional techniques, such as with the RAMP system (DuPont DeNemours & Co.), which applies Fmoc chemistry. Alternatively, recombinant peptides or immunoglobulin heavy chains (or portions thereof) containing the migis epitopes may be biosynthesized by expressing in E. coli or mammalian cells the gene segments containing the coding sequence of these peptides.

When using a synthetic or recombinant peptide segment as an immunogen, it is usually more effective to conjugate it to a protein carrier, for example, hepatitis B surface antigen, core antigen, or preferably keyhole lympit hemocyanin (KLH). If the peptidic segment lacks a lysine residue or if the lysine residue is in the middle part of the segment, it is desirable to add a lysine residue at the C-terminal end. Because the N-terminus already has an α-amino group, the modified synthetic peptidic will have two available amino groups for linking.

Multiple molecules of peptides can be conjugated to each molecule of the carrier protein. With KLH, a preferred molar ratio for peptide/KLH is 10. The method of conjugation is very well established. Cross-linkers such as gluteraldehyde or bis (sulfosuccinimidyl) suberate or preferably disulfosuccinimidyl tartarate (Catalogue #21579, 20591, Pierce Chemical Co., Rockford, IL) can be used.

As immunogens, these peptides can be used to make monoclonal antibodies which are specific for them, using the protocal described further below. A specific example of making monoclonal antibodies to the migis epitope of human ε chain appears in U.S. Patent application, Ser. No. 07/468,766, filed Jan. 23, 1990, the disclosure being incorporated herein by reference. Such immunogenic peptides can also be used to immunize rabbits, goats, rats, or mice (or even anther human being) to prepare polyclonal antibodies to the extracellular migis epitopes. The monoclonal antibodies to the peptides of the invention will react, in vivo, only with the exposed and accessible extracellular migis epitopes on the membrane bound immunoglobulins, and not with the secreted immunoglobulins. The polyclonal antibodies will also react with the extracellular migis epitopes, although not exclusively.

When preparing monoclonal antibodies, it is not necessary to use the synthetic or recombinant peptides in both immunization and antibody identification. For example, in immunizing mice for preparing spleen cells for fusion with myeloma cells, the immunogen may be the membrane-bound immunoglobulin isolated from the plasma membrane of immunoglobulin-bearing myeloma cells, such as SK007 cells, or it may be the myeloma cells themselves. Transfectomas, which are developed by transfecting mouse myeloma cells with genes of human immunologlobulin heavy chains and light chains and which express on their cell surface membrane-bound immunoglobulins, may also be used as immunogens. For initial monoclonal antibody identification following immunization, the aforementioned synthetic peptides conjugated to ovalbumin or bovine serum albumin, which are not used as carrier proteins in immunization, are preferably used.

Lymphocytes from the spleen or lymph nodes of immune mice and rats can also be used to prepare hybridomas secreting monoclonal antibodies specific for the extracellular migis epitopes. A preferred protocol for preparing monoclonal antibodies is to fuse immune spleen cells of mice with non-secreting mouse myeloma cells, such as NS-1 or SP2/0 cells, using polyethylene glycol.

A preferred immunization protocol for preparing monoclonal antibodies is to inject into each mouse 50 μg of the peptide-KLH conjugate in complete Fruend's adjuvant. Two and four weeks later, the same amount of antigen is given subcutaneously in incomplete Fruend's adjuvant. After about six weeks, the fourth antigen injection is given intraperitoneally in saline. Mice are sacrificed 4 days after the last injection and the spleens are removed for preparing single cell suspensions for fusion with myeloma cells.

A similar protocol can be used for immunization with purified native human membrane-bound immunoglobulins (having attached membrane anchoring peptide segments) isolated from the plasma membrane of immunoglobulin-bearing human myeloma cells, such as SK007 cells. When human immunoglobulin-bearing cells are used as the immunogen, $1 \times 10^7$ cells are injected intraperitoneally at two week intervals.

The fusion procedure with polyethylene glycol and other various procedures concerning cloning and hybridoma culturing have been well established. The preferred protocol is the well-known one described by Hudson, L and Hay. F.C. (Practical Immunology, 2nd edition, pp. 303-313, 1980, Blackwell Publishing Co., Boston).

The screening of hybridomas for monoclonal antibodies (or the identification of polyclonal antibodies) reactive with the extracellular migis epitopes of the invention can be performed with an enzyme linked immunosorbent assay (ELISA) using the synthetic peptide as the solid phase antigen. An alternative solid phase antigen is the conjugate of a membrane anchoring peptide with a carrier protein different from that used in the immunogen, such as bovine serum albumin or ovalbumin.

Monoclonal antibodies specific for the extracellular migis epitopes can be used to reduce or eliminate the tumorous B cells by antibody-dependent cellular cytotoxicity (ADCC), complement-mediated cytolysis, or other cytolytic or regulatory immune mechanisms. These monoclonal antibodies can also be used as effector agents mediating an immune function or as targeting agents for cytotoxic cells.

The monoclonal antibodies of the invention can also be used as carrier agents of toxins or cytotoxic drugs or for delivering an effector substance. These monoclonal antibodies can be conjugated to immunotoxins. The immunotoxin-antibody conjugate will bind and directly kill B cells producing antibody of a specific isotype and not B-cells producing uninvolved isotypes. These immunotoxins are cytolytic or cytotoxic agents, including cytotoxic steroids, gelonin, abrin, ricin, PseudoNonas toxin, diptheria toxin, pokeweek antiviral peptide, tricathecums, radioactive nuclides, and membrane-lytic enzymes (such as phospholipases). The antibody and the agent can be conjugated by chemical or by genetic engineering techniques.

The immunotoxin-antibody conjugates are another therapeutic alternative for treating B cell lymphoma or leukemia. The immunotoxins may be used alone or in combination with the free antibodies of the invention.

Another alternative is to produce chimeric antibodies (having an animal variable region and a human constant region), or fragments thereof, or use human genomic expression libraries (Stratagene Corp., La Jolla, California), to produce fragments of human antibodies and then construct whole human antibodies using techniques similar to those for producing chimeric antibodies. Such chimeric antibodies or human antibodies, or fragments of either, are less immunogenic than other mammalian equivalents, and therefore better suited for in vivo administration.

The antibodies of the invention (and the conjugates and other derivatives) are administered systemically, and preferably intravenously. They can be administered in any pharmaceutically acceptable vehicle.

Derivative therapies based on the antibody therapy of the invention can also be used. For example, antibodies of certain IgG subclasses, such as mouse IgG2a and human IgG1 and IgG3, can mediate ADCC carried out by certain Fc receptor-bearing phagocytic leukocytes. Administration of such mouse gamma 2a antibodies, chimeric antibodies bearing human gamma-1 or gamma-3 chains, or human IgG1 or IgG3 antibodies can be used to down-regulate or lyse tumorous B cells of a particular isotype. These antibodies can be administered to patients afflicted with B cell lymphoma or leukemia in amounts sufficient to lyse substantially all the B cells which express immunoglobulin of the involved isotypic class, and consequently, to reduce substantially the tumorous cells.

Another therapeutic alternative involves active immunization, meaning that antibodies specific to the extracellular migis epitopes are endogenously produced in vivo. These endogenously produced antibodies bind the migis epitopes and cause destruction of the associated B cells. Production of such antibodies can be induced either by introducing an immunogenic membrane anchoring peptide of the invention, or a paratope-specific, anti-idiotypic antibody. Anti-idiotype antibodies against the paratope of the antibodies of the invention conformationally resemble the extracellular migis epitopes. These anti-idiotypic antibodies can be used to actively immunize against the migis epitopes and induce the endogenous formation of antibodies against the migis epitopes.

Such paratope-specific, anti-idiotyptic antibodies are administered to a patient suffering from B cell lymphoma or leukemia in an immunogenic amount sufficient to induce the formation of antibodies against the targeted B cell. These anti-idiotypic antibodies are preferably administered as chimeric antibodies or human antibodies. They may also be antibody fragments (which also may be chimeric or human in nature).

Certain factors, such as GM-CSF (granulocyte monocute-colony stimulation factor) or M-CSF (monocute-colony stimulation factor), are known to induce the proliferation of leukocytes, including those mediating ADCC. In in vitro experiments, GM-CSF and M-CSF have been shown to augment the ADCC activity on tumor cells mediated by monoclonal antibodies specific for surface antigens expressed on the tumor cells. The therapeutic effect of specific monoclonal antibodies of the invention, conjugates, or polyclonal antibodies in treating B cell lymphoma or leukemia should be enhanced by combining the use of factors that augment ADCC activities.

Derivative antibodies can be made which draw cytotoxic cells such as macrophages or cytotoxic T cells toward the targeted Ig-bearing B cells. These derivative antibodies include bi-specific antibodies having a specificity for a receptor of a cytotoxic cell and a specificity for the targeted Ig bearing B cells. Such hybrid bi-specific antibodies can include two different Fab moieties, one Fab moiety having antigen specificity for the target migis epitopes and the other Fab moiety having antigen specificity for a surface antigen of a cytotoxic cell, such as CD3 or CD8. The bi-specific antibodies of the invention can be a single antibody having two specificities, or a heteroaggregate of two or more antibodies or antibody fragments. See, &.&., C. Reading, U.S. Pat. Nos. 4,474,893 and 4,714,681; Segal et al., U.S. Pat. No. 4,676,980.

While monoclonal antibodies of the invention can be used for in vivo applications, they may also be used in extra-corporeal ex-vivo applications. The tumorous B cells in the circulation of the patients can be removed by an affinity matrix (antibody immobilized on a solid phase) which is conjugated with the monoclonal antibodies of the invention.

Another use for the antibodies of the invention is for determining numbers and relative proportions of B lymphocytes bearing particular isotypes in n-fixed leukocyte populations. The migis specific antibodies will not react with cells which bear secreted immunoglobulins via such cells' Fc receptors. Such cells include macrophages and activated T cells. The profile of the B cells may indicate the immune status of the individual. The same information can also indicate how much antibody is needed to deplete a substantial portion of B cells bearing a particular isotype, where some of those B cells are tumorous. For this purpose, antibodies can be used in standard assays which are used to determine cell surface antigens. In general, the antibodies are contacted with a sample of the leukocytes to be tested under conditions which allow the antibodies to bind isotype-bearing cells in the sample. The cells are then examined for binding of antibody. This can be accomplished by conventional cell staining procedures, for example, a fluorescently labeled second antibody can be used to detect binding of antibody.

A. Sequences of Human IF-D and IgM

The sequences of the extracellular segments of human IgD and IgM membrane anchoring peptides were previously known, and are respectively as follows:

| | |
|---|---|
| Human IgM | EGEVS.ADEEG.FEN |
| Human IgD | YLAMT.PLIPQ.SKDEN.SDDYT.TFDDV.GS |

The features and properties of the various segments of the whole human IgD and IgM membrane anchoring peptides are as follows:

| | First Segment | Middle Segment | Last Segment | TOTALS |
|---|---|---|---|---|
| Properties: | Hydrophilic Highly Acidic | Hydrophobic No charged Residues | Hydrophilic | |
| Physical Location: | On exterior surface | In membrane lipid bilayer | On cytoplasmic surface | |
| Human IgM* | 13 | 25 | 3 | 41 |
| Human IgD* | 27 | 25 | 3 | 55 |

*The numbers represent the number of amino acid residues.

B. εChain Membrane Anchoring Peptide

The manner in which the proposed sequence of one E chain membrane anchoring peptide was determined is set forth in detail in U.S. Patent application Ser. No. 07/468,766, filed Jan. 23, 1990, the teachings of which are incorporated herein by reference. In brief, the approach was to obtain a DNA clone with genes encoding the membrane anchoring peptides through screening the human genomic library. The reagents and methods needed for this screening are also described in U.S. Pat. application Ser. No. 07/468,766.

Another approach which can be used to construct a CDNA library from the mRNA preparation of a human myeloma cell line which expresses IgE on the surface. The cDNA library is then screened with four different DNA probes for clones containing the extracellular membrane anchoring peptide segment.

An alternative and complementary method of sequencing the IgE membrane anchoring peptides is to amplify its associated MRNA with the polymerase chain reaction (PCR) technology to produce a high proportion of corresponding DNA. The resulting DNA is then purified by gel electrophoresis and subjected to sequence analysis. The primers and reagents needed for this PCR are described in U.S. Pat. application Ser. No. 07/468,766.

The nucleotide sequence of the DNA segment encompassing the encoding segments for one proposed isoform of membrane anchoring peptide of human membrane bound ε chain was determined, and is shown in FIGS. 1 and 2A. FIG. 2A also shows the deduced amino acid sequence of this segment. The membrane two exons (εm1 and εm2) can be seen in FIG. 2A. The extracellular portion is identified as the first fifteen amino acids encoded by the membrane exon 1, indicated by bold letters in FIG. 2A. This precedes a stretch of about 25 hydrophobic amino acids which form the transmembrane region, indicated by the underlined amino acid sequence in FIG. 2A. Two possible structures of this extracellular portion are shown below:

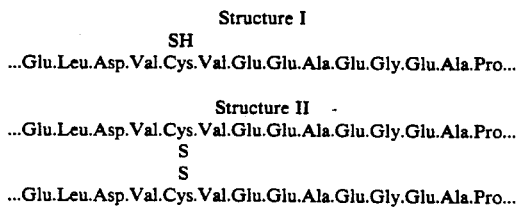

C. Alternative MRNA Splicings of Human ε Chain in the Membrane Exon Region

Alternative MRNA splicings in the human e chain membrane exon region can yield other peptide isoforms. Two other isoforms (II and III) resulted from alternative splicings of the MRNA which produced the first ε chain anchoring peptide (isoform 1) described above and shown in FIG. 2A. These two alternative RNA splicings are shown schematically in FIG. 1, and the nucleotide and proposed amino acid sequences are shown in FIGS. 2B, and 2C.

Alternative splicings are defined as a splicing other than the splicing of the CE4 exon to the εm1 exon to the εm2 exon, which produces isoform I. As seen in FIG. 2A, isoform I contains a peptide which presumbably spans through the membrane liquid bilayer and has 67 amino acid residues, 15 of which are presumed to be extracellular and which form, in whole or in part, the migis epitopes. Referring to FIG. 2B, isoform II has 119 amino acid residues, 67 of which are presumed to be extracellular. It is also possible that isoform 111, which, as shown in FIG. 2C, has 45 amino acid residues, is associated with the B cell surface via a cell surface receptor. Tie method of determining the nucleotide sequence of isoform 11 and Ill is outlined below and described in detail in U.S. Pat. application Ser. No. 07/515,604, filed Apr. 27, 1990, the teachings of which are incorporated herein by reference.

The nucleotide sequencing was performed on the CDNA derived from MRNA isolated from human cells expressing membrane-bound IgE. A commercially available human IgE expressing myeloma, SKO-007 (from the ATCC), was used.

The segments of CDNA derived from MRNA regarded as pertinent to identification and characterization of the transmembrane regions of human E chain were amplified by PCR, as described further below, using oligonucleotide primers having sequences corresponding to segments in CH4 and in regions of the membrane exons. The four oligonucleotide primers used, and their locations, were as follows:

1) 5'CAGAATTCAGATGAGT-rCATCTGCCGTGC3' located in CH4 domain;

2) 5'GGAGGAATrCGTrGGTGTAGTCGA3' located in εm2 domain (complementary strand was used);
3) 5'GCGAATTCGATGCAGAGGCCGGT-CCACG3' located in εm1 domain (complementary strand was used);
4) 5'CTCGGCAGTCCCTGCTGCTGT3' located in the segment upstream from εm1 exon, referred to as εm0 segment in FIG. 1 (complementary strand was used).

The nucleotide sequencing of the various CDNA clones revealed two alternative splicings, in addition to the one previously described above and shown in FIG. 2A. The first alternative MRNA splicing yields isoform II shown in FIGS. 1 and 2B. It results from linking the CH4 domain at the same expected donor site to an acceptor site 156 bp upstream of the εm1 exon. This alternative splicing results in MRNA that contains both the εm1 segment and the εm2 exon in the same reading frame as the conventional mRNA. It has the structure corresponding to that wherein the Cε4 exon is linked to a new exon (the εm1' exon) which is linked to the εm2 exon. The εm1' exon is 278 bp long, being composed of εm0 segment (156 bp) and εm1 segment (122 bp). The translated ε peptide corresponding to this alternative splicing would have 52 extra amino acid residues, as indicated by the bold-faced amino acid residues in FIG. 2B.

A second alternate MRNA splicing yields isoform III shown in FIGS. 1 and 2C. It results from linking the CH4 domain at the expected splicing donor site directly to εm2 domain, leaving out εm1 domain. The reading frame of εm2 is shifted by one bp and encodes for a peptide having a different sequence and a different length from the one encoded by the original εm2 exon. This new exon (referred to as εm2') has 137 bp (including the TGA termination codon) and encodes for 45 amino acid residues (the bold-faced peptide segment in FIG. 2C). Isoform III does not have a clear transmembrane segment, which is usually characterized by a stretch of 25 hydrophobic or noncharged amino acid residues. Nevertheless, this peptide of 45 amino acid residues in length may function as an extracellular migis segment, as it may be anchored to the cell surface by phosphatidylinositol glycan mechanism.

D. Membrane Anchoring Peptides of Human gamma Chain (1) Extracellular Migis Segments and Uses Therefor The genomic DNA sequences of the membrane anchoring segments of human gamma-1, gamma-2, gamma-3, gamma-4, were determined by the methods described below. Two membrane exons encode for these DNA sequences. In FIGS. 3A, 3B, respectively, the genomic nucleotide sequences corresponding to the two membrane exons of human gamma-1 are underlined. The upper case letters in FIG. 4A denote the genomic DNA sequence of these two membrane exons for human gamma-1, gamma-2, gamma-3, and gamma-4, the flanking nucleotide sequences being indicated by lower case letters. FIG. 4B shows the deduced amino acid sequences encoded by the exons of FIG. 4A. FIG. 5A shows the CDNA sequence of a segment of human gamma-1 chain which includes the two membrane exons and some flanking sequences. FIG. 5B depicts the splicing donor sites and acceptor sites involved in the formation of the segment shown in FIG. 5A.

Based on the genomic DNA sequences, CDNA sequences, and the identified splicing mechanisms, the predicted amino acid sequences of the membrane anchoring peptides of human gamma-1, gamma-2, gamma-3, and gamma-4 shown in FIG. 4B were determined. By comparing to the sequences of membrane anchoring peptides of other known immunoglobulins, the hydrophobic stretch that presumably spans through the membrane lipid bilayer can be identified. This sequence of 25 amino acid residues is LWTTI-TIFIT-LFLLS-VCYSA-TVTFF(gamma-1). To the N terminal end of this hydrophobic stretch is the segment proposed to form the migis epitopes. Thus for human gamma-1, gamma-2, gamma-3, and gamma-4 chains, the sequence of 18 amino acid residues (as shown in FIG. 4B) which form the extracellular migis epitope, entirely or in part, is:

ELOLE - ESCAE AQDGE LDG.

These proposed migis epitopes are believed to be extracellular and accessible by antibodies. They all have the same lengths (18 amino acid residues) and have multiple acidic residues, suggesting that the gamma migis segments are also hydrophilic and CL, extracellular. Since the peptides for human gamma-1, gamma-2, gamma-3, and gamma-4 are identical, it is likely a monoclonal antibody can be prepared which recognizes cell-bound but not secreted IgG of all four subclasses.

(ii) The Human gamma mus Segments

The proposed sequence of the membrane anchoring peptides of human gamma chains was determined by the methods set forth below. Like genomic DNA clones containing human a1 or a2 sequences, the genomic DNA clones containing gamma-1, gamma-2, gamma-3, and gamma-4 can be obtained from a genomic DNA library, such as lambda - FIX phage library of genomic DNA of human lung fibroblast line, W138, provided by Strategene (LaJolla, California). The human genomic gamma-1, gamma-2, gamma-3, and gamma-4 DNA segments, which were originally provided by Dr. Sherrie Morrison (previously of Columbia University and now of the University of California, Los Angeles), were used for constructing chimeric reurine $V_{H9}V_L$/human $C_{gamma}$ genomic DNA. The human B cell line, IM9, expressing IgG1 on the surface was obtained from American Type Culture Collection, Rockville, Maryland. Peripheral blood mononuclear cells from normal blood donors were used as a source of mRNA for examining human gamma chain sequences. The various restriction enzymes used were from Boehringer Mannheim, New England Biolabs and Bethesda Research Laboratories. The Erase-abase kit, which can be used to construct nested deletions, was obtained from Promega Corp. Dideoxysequencing of double stranded templates was performed using T7 sequencing kit from Pharmacia/LKB. ne Bluescript vector was obtained from Strategene Cloning Systems. All clones were DH5αF' cells (Bethesda Research Laboratory).

To facilitate mapping and sequencing, the genomic gamma clones were subcloned into Bluescript SK II+. In order to locate the membrane regions, a set of the nested deletions was created using the Erase-abase kit. The izamma plasmid was cut with Sacl and Ncol. Sacl gives 5' recessed ends which are protected from Exo III digestion. Several μg were digested with Exo III and aliquots were withdrawn at 30 second intervals. These aliquots were placed in S1 digestion mix, which stops the Exo III reaction. After 30 minutes, the S1 reaction was stopped by heating to 70° C. Following a brief treatment with Klenow fragment, each aliquot was recircularized with T4 DNA ligase. Plasmids with deletions of various lengths were sequenced and compared to mouse gamma chain membrane regions. After identifying clones which contain a part of the membrane regions, oligonucleotide primers were constructed to complete the sequencing of segments covering the membrane exons.

For sequencing CDNA, the CDNA clones were prepared from CDNA synthesized from RNA isolated from IM9 cells or peripheral blood mononuclear cells from normal donors, by using a primer in the 3'untranslated region 5'GTTGAGGGCGGTGAGACG3' (complementary sequence from genomic DNA) and AMV reverse transcriptase. The RNA isolation and CDNA preparation were performed according to *Molecular Cloning*, (Sambrook, Fritch, and Maniatis, Cold Spring Harbor, 1989). Second strand synthesis and amplification of desirable gene segments was carried out using PCR with a 3' primer, 5'GGCAACTGCGAGG-CCAGAG3' from the 3' untranslated region and a primer with the sequence from the CH3 domain (5'AGAAGAGCCTC-TCCCTGTC3'). The PCR conditions were as follows: denaturation, 94° C., 1 min; annealing, 60° C., 2 min; polymerase reaction, 72° C., 3.5 min; 35 cycles.

Two bands of 350 and 500 nucleotides were isolated from IM9 RNA source. These were cloned into Bluescript SK II+. Upon sequencing, clones with 350 bp inserts having gamma-I sequences were identified. This CDNA was labeled with $^{32}$p and used to screen by colony hybridization a number of CDNA clones derived from the PCR product of RNA from normal lymphocytes. The inserts of the positive clones were prepared and the nucleotide sequences determined.

E. Membrane Anchoring Peptides of Human α Chain

The DNA sequence corresponding to human IgA membrane anchoring peptide was determined as outlined below and is described in detail in U.S. Pat. application Ser. No. 07/455,080, filed Dec. 22, 1989, the teachings of which are incorporated herein by reference. The genomic DNA sequence of human α1 and the deduced amino acid sequence are shown in FIG. 6. The initial 74 nucleotides in lower case letters represent the end of the known and published α1 genomic DNA sequence. There are two proposed isoforms of human membrane-bound α1. The two isoforms result from the use of two different MRNA splicing acceptor sites (indicated by the arrows): one from the predicted acceptor site, 5'TTGCAGA3', which corresponds to an existing site in the murine α gene; one from an acceptor site, 5'TGGCAGG3', 18 nucleotides upstream in the same reading frame. The two α1 isoforms, respectively, are deduced to have 65 and 71 amino acid residues in the membrane anchoring peptide region. The 6 extra amino acid residues in the longer isoform are indicated by the lower case letters in FIG. 6, where the underlined amino acid residues indicate the proposed extracellular region of the membrane anchoring peptide. This region is predicted to be extracellular based on the fact that it contains a high proportion of acidic residues. The extracellular regions will include the migis epitopes.

FIG. 7A shows the nucleotide sequences and FIG. 7B shows the corresponding amino acid sequences of the membrane anchoring peptides (the longer isoform indicated by the additional lower case letters) of human α1 and α2 compared with murine α. The underlined portion of FIG. 7B represents the proposed extracellular segment. It can be seen that the human and murine membrane anchoring peptides are homologous. It can also be seen that the shorter isoforms of human α1 and α2 differ by only one amino acid residue, and that the longer isoforms of human α1 and α2 differ by a total of two amino acid residues.

The DNA sequence of the ct chain membrane anchoring peptides was determined by comparing the sequence of the segment amplified from genomic DNA with that of a murine α membrane exon, and from CDNA prepared from RNA of an IgA-expressing human cell line, DAKIKI. The procedure to obtain the membrane exon was to start with the human genomic DNA library (purchased from Stratagene, La Jolla California), to screen for clones positive for either the α1 or α2 gene segments, to amplify these genomic DNA segments, and to separate the segments by gel electrophoresis. The segment of interest (determined by comparison with the corresponding murine segment) was then sequenced. The 3' end of this segment ended in the middle of the predicted membrane exon. The sequences for the remainder of the membrane exon and the 3' untranslated region were obtained by subcloning and sequencing of additional lambda clones containing segments flanking the membrane exons. These clones were identified by Southern blot analysis using a probe from the membrane exon. As noted above, these sequencing procedures are described in detail in U.S. Pat. application Ser. No. 07/455,080.

F. Developing Monoclonal Antibodies Against migis Epitopes

The determination of nucleotide sequences of genomic and CDNA segments covering the membrane exon regions of the various isotypes of human heavy chains described above have provided the deduced amino acid sequences of the extracellular segments of the membrane anchoring peptides of the membrane-bound heavy chains. Synthetic peptides with sequences representing the extracellular segments of the membrane anchoring peptides have allowed the development of murine monoclonal antibodies against the migis epitopes.

Using the methods described in U.S. Pat. application, Ser. No. 07/468,766, filed on Jan. 23, 1990 and its predecessor related patent applications, monoclonal antibodies against the migis epitope of human IgE were developed. As described in application Ser. No. 07/468,766, mice were immunized with a transfectoma cell line, SE44, derived from a mouse myeloma and expressing human IgE on the surface. Other hybridomas were also developed by using B cells from mice which had been immunized with both migis-ε peptide-ovalbumin conjugate and with SE44 cells. The migis-ε peptide is a dimer of the peptide described in Section B above.

The monoclonal antibody E46-13-3 specific for a migis-ε epitope was found in ELISA to bind to migis-ε peptide coupled to ovalbumin or KLH, but not to bind to any significant extent to ovalbumin or KLH coupled by migis-gamma, migis-α, misis-μ, and migis-δ peptides. The antibody also did not bind to ovalbumin coupled with irrelevant peptides, such as a 15-mer synthetic peptide having a sequence from a segment of gp120 of HIV-1.

In additional tests with fluorescence flow cytometric analyses, E46-13-3 was found to bind to SE44 cells, but not to its transfection parent, ie., Sp2/0 murine myeloma cells. The only difference between the two cell lines was presumably the fact that the SE44 expressed chimeric IgE bearing the human ε constant region. The antibody E46-13-3 also did not bind to an IgG-expressing cell line, IM9, or an IgA-expressing cell line, DAKIKI.

From the mice immunized with migis-ε-KLH conjugate and SE44 cells, monoclonal antibody HEM 2.11 was developed. This antibody has all the specificities of E46-13-3. In addition, it was shown that HEM 2.11 could react with membrane bound δ chain in Western blot analyses. The binding of HEM 2.11 to SE44 cells and SKO-007 cells (which also express human IgE) could be inhibited by free migis-ε peptide.

Among the extracellular migis peptides of various isotypes, migis-ε, of 15 amino acid residues, is among the shortest. Human migis-ε peptide also bears a very high homology with mouse migis-ε peptide. The successful development of monoclonal antibody against the human migis-ε epitopes demonstrates the accessibility of the migis-ε epitopes. Given the short length of human migis-ε peptides in comparison with the other isotypes, this indicates that the migis epitopes of other isotypes will also be accessible. The development of monoclonal antibodies against human misis-ε peptide further indicates the feasibility of preparing monoclonal antibodies against migis epitopes of the other isotypes.

It should be understood that the foregoing embodiments, procedures and products are exemplary only and not limiting, that the scope of protection is defined only in the following claims, and that it includes all equivalents of the subject matter of those claims.

What is claimed is:

1. A peptide of the amino acid sequence of the extracellular segment of human γ chain.

2. The peptide of claim 1 conjugated to a substance which increases the immunogenicity of the peptide.

3. The peptide of claim 2 wherein the substance is hepatitis B surface antigen, core antigen, or keyhole limpet hemocyanin.

* * * * *